(12) United States Patent
Lizardi et al.

(10) Patent No.: US 9,078,646 B2
(45) Date of Patent: Jul. 14, 2015

(54) KNOTLESS SUTURE ANCHOR

(71) Applicant: DePuy Mitek, LLC, Raynham, MA (US)

(72) Inventors: Jose E. Lizardi, Walpole, MA (US); Mehmet Ziya Sengun, Canton, MA (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

(21) Appl. No.: 14/078,660

(22) Filed: Nov. 13, 2013

(65) Prior Publication Data
US 2014/0107701 A1 Apr. 17, 2014

Related U.S. Application Data

(62) Division of application No. 12/909,355, filed on Oct. 21, 2010, now Pat. No. 8,613,756.

(51) Int. Cl.
*A61B 17/04* (2006.01)
*A61B 17/00* (2006.01)

(52) U.S. Cl.
CPC ... *A61B 17/0401* (2013.01); *A61B 2017/00004* (2013.01); *A61B 2017/045* (2013.01); *A61B 2017/0414* (2013.01); *A61B 2017/0424* (2013.01); *A61B 2017/0425* (2013.01); *A61B 2017/0432* (2013.01); *A61B 2017/0433* (2013.01); *A61B 2017/0438* (2013.01); *A61B 2017/0445* (2013.01); *A61B 2017/0448* (2013.01)

(58) Field of Classification Search
USPC ........... 606/60, 104, 144, 148, 232, 301, 313, 606/916; 623/13.11, 13.13, 13.14, 13.18
See application file for complete search history.

(56) References Cited

U.S. PATENT DOCUMENTS

| | | |
|---|---|---|
| 4,590,928 A | 5/1986 | Hunt |
| 4,772,286 A | 9/1988 | Goble |
| 4,778,468 A | 10/1988 | Hunt |
| 4,851,005 A | 7/1989 | Hunt |
| 5,013,316 A | 5/1991 | Goble |
| 5,037,422 A | 8/1991 | Hayhurst |
| 5,236,445 A | 8/1993 | Hayhurst |
| 5,268,001 A | 12/1993 | Nicholson |
| 5,324,308 A | 6/1994 | Pierce |
| 5,354,298 A | 10/1994 | Lee |
| 5,380,334 A | 1/1995 | Torrie |
| 5,464,427 A | 11/1995 | Curtis |
| 5,472,452 A | 12/1995 | Trott |
| 5,480,403 A | 1/1996 | Lee |
| 5,584,835 A | 12/1996 | Greenfield |
| 5,601,558 A | 2/1997 | Torrie |
| 5,643,321 A | 7/1997 | McDevitt |
| 5,649,963 A | 7/1997 | McDevitt |

(Continued)

FOREIGN PATENT DOCUMENTS

| | | |
|---|---|---|
| EP | 1884199 A1 | 2/2008 |
| WO | WO 01/10312 A1 | 2/2001 |

*Primary Examiner* — Dianne Dornbusch
*Assistant Examiner* — Robert Lynch

(57) ABSTRACT

A suture anchor is disclosed having an outer body with an axial bore which receives and inner body for rotation. Suture passes between the inner body and outer body and rotation of the inner body wraps the suture thereabout locking the suture thereto. Rotation of the inner body also effects radial expansion of at least a portion of the outer body to engage to anchor into a bone hole.

5 Claims, 9 Drawing Sheets

(56) References Cited

U.S. PATENT DOCUMENTS

| | | |
|---|---|---|
| 5,690,676 A | 11/1997 | DiPoto |
| 5,707,395 A | 1/1998 | Li |
| 5,713,903 A | 2/1998 | Sander |
| 5,720,753 A | 2/1998 | Sander |
| 5,720,765 A | 2/1998 | Thal |
| 5,782,865 A | 7/1998 | Grotz |
| 5,797,963 A | 8/1998 | McDevitt |
| 5,814,071 A | 9/1998 | McDevitt |
| 5,899,921 A | 5/1999 | Caspari |
| 5,902,321 A | 5/1999 | Caspari |
| 5,935,129 A | 8/1999 | McDevitt |
| 5,948,000 A | 9/1999 | Larsen |
| 5,948,001 A | 9/1999 | Larsen |
| 5,957,953 A | 9/1999 | DiPoto |
| 5,980,558 A | 11/1999 | Wiley |
| 6,045,574 A | 4/2000 | Thal |
| 6,086,608 A | 7/2000 | Ek |
| 6,126,663 A | 10/2000 | Hair |
| 6,143,017 A | 11/2000 | Thal |
| 6,200,329 B1 | 3/2001 | Fung |
| 6,267,766 B1 | 7/2001 | Burkhart |
| 6,280,474 B1 | 8/2001 | Cassidy |
| 6,290,711 B1 | 9/2001 | Caspari |
| 6,355,044 B1 | 3/2002 | Hair |
| RE37,963 E | 1/2003 | Thal |
| 6,520,980 B1 | 2/2003 | Foerster |
| 6,524,317 B1 | 2/2003 | Ritchart |
| 6,527,794 B1 | 3/2003 | McDevitt |
| 6,540,750 B2 | 4/2003 | Burkhart |
| 6,544,281 B2 | 4/2003 | ElAttrache |
| 6,562,071 B2 | 5/2003 | Järvinen |
| 6,575,976 B2 | 6/2003 | Grafton |
| 6,585,730 B1 | 7/2003 | Foerster |
| 6,632,245 B2 | 10/2003 | Kim |
| 6,641,596 B1 | 11/2003 | Lizardi |
| 6,641,597 B2 | 11/2003 | Burkhart |
| 6,652,560 B1 | 11/2003 | Gerke |
| 6,660,023 B2 | 12/2003 | McDevitt |
| 6,692,516 B2 | 2/2004 | West, Jr. |
| 6,736,847 B2 | 5/2004 | Seyr |
| 6,770,076 B2 | 8/2004 | Foerster |
| 6,780,198 B1 | 8/2004 | Gregoire |
| 6,818,010 B2 | 11/2004 | Eichhorn |
| 6,840,953 B2 | 1/2005 | Martinek |
| 6,855,157 B2 | 2/2005 | Foerster et al. |
| 6,923,824 B2 | 8/2005 | Morgan |
| 6,939,379 B2 | 9/2005 | Sklar |
| 7,037,324 B2 | 5/2006 | Martinek |
| 7,074,203 B1 | 7/2006 | Johanson |
| 7,081,126 B2 | 7/2006 | McDevitt |
| 7,083,638 B2 | 8/2006 | Foerster |
| 7,090,690 B2 | 8/2006 | Foerster |
| 7,144,415 B2 | 12/2006 | Del Rio |
| 7,201,754 B2 | 4/2007 | Stewart |
| 7,247,164 B1 | 7/2007 | Ritchart |
| 7,309,346 B2 | 12/2007 | Martinek |
| 2001/0051807 A1 | 12/2001 | Grafton |
| 2002/0007182 A1 | 1/2002 | Kim |
| 2002/0013608 A1 | 1/2002 | ElAttrache |
| 2002/0052629 A1 | 5/2002 | Morgan |
| 2002/0095180 A1 | 7/2002 | West |
| 2002/0111653 A1 | 8/2002 | Foerster |
| 2002/0128684 A1 | 9/2002 | Foerster |
| 2002/0143364 A1 | 10/2002 | Burkhart |
| 2002/0156490 A1 | 10/2002 | Enayati |
| 2003/0004545 A1 | 1/2003 | Burkhart |
| 2003/0065390 A1 | 4/2003 | Justin |
| 2003/0130695 A1 | 7/2003 | McDevitt |
| 2003/0149448 A1 | 8/2003 | Foerster |
| 2003/0153921 A1 | 8/2003 | Stewart |
| 2003/0191530 A1 | 10/2003 | Sklar |
| 2003/0195563 A1 | 10/2003 | Foerster |
| 2003/0233095 A1 | 12/2003 | Urbanski |
| 2004/0068262 A1 | 4/2004 | Lemos |
| 2004/0088004 A1 | 5/2004 | Rosch |
| 2004/0098050 A1 | 5/2004 | Foerster |
| 2004/0098052 A1 | 5/2004 | West |
| 2004/0133239 A1 | 7/2004 | Singhatat |
| 2004/0172062 A1 | 9/2004 | Burkhart |
| 2004/0243179 A1 | 12/2004 | Foerster |
| 2004/0260345 A1 | 12/2004 | Foerster |
| 2004/0267361 A1 | 12/2004 | Donnelly |
| 2005/0033364 A1 | 2/2005 | Gregoire |
| 2005/0075668 A1 | 4/2005 | Lizardi |
| 2005/0090862 A1 | 4/2005 | McDevitt |
| 2005/0149122 A1 | 7/2005 | McDevitt |
| 2005/0216059 A1 | 9/2005 | Bonutti |
| 2005/0228413 A1 | 10/2005 | Binmoeller |
| 2005/0240226 A1 | 10/2005 | Foerster |
| 2005/0245932 A1 | 11/2005 | Fanton |
| 2005/0267479 A1 | 12/2005 | Morgan |
| 2005/0277986 A1 | 12/2005 | Foerster |
| 2006/0015107 A1 | 1/2006 | Sklar |
| 2006/0100628 A1 | 5/2006 | Martinek |
| 2006/0106422 A1 | 5/2006 | Del Rio |
| 2006/0106423 A1 | 5/2006 | Weisel |
| 2006/0116719 A1 | 6/2006 | Martinek |
| 2006/0235413 A1 | 10/2006 | Denham |
| 2006/0271105 A1 | 11/2006 | Foerster |
| 2006/0276841 A1 | 12/2006 | Barbieri |
| 2006/0282081 A1 | 12/2006 | Fanton |
| 2006/0282082 A1 | 12/2006 | Fanton |
| 2006/0282083 A1 | 12/2006 | Fanton |
| 2007/0005068 A1 | 1/2007 | Sklar |
| 2007/0032793 A1 | 2/2007 | Del Rio |
| 2007/0038221 A1 | 2/2007 | Fine |
| 2007/0093858 A1 | 4/2007 | Gambale |
| 2007/0142861 A1 | 6/2007 | Burkhart |
| 2007/0156148 A1 | 7/2007 | Fanton |
| 2007/0156149 A1 | 7/2007 | Fanton |
| 2007/0156150 A1 | 7/2007 | Fanton |
| 2007/0156176 A1 | 7/2007 | Fanton |
| 2007/0191849 A1 | 8/2007 | ElAttrache |
| 2007/0203498 A1 | 8/2007 | Gerber |
| 2007/0219557 A1 | 9/2007 | Bourque |
| 2007/0219558 A1 | 9/2007 | Deutsch |
| 2007/0225719 A1 | 9/2007 | Stone |
| 2007/0260259 A1 | 11/2007 | Fanton |
| 2008/0004659 A1 | 1/2008 | Burkhart |
| 2008/0009904 A1 | 1/2008 | Bourque |
| 2008/0015594 A1 | 1/2008 | Ritchart |
| 2008/0033486 A1 | 2/2008 | Whittaker |
| 2008/0051836 A1 | 2/2008 | Foerster |
| 2008/0077161 A1 | 3/2008 | Kaplan |
| 2008/0086138 A1 | 4/2008 | Stone |
| 2008/0306510 A1 | 12/2008 | Stchur |
| 2009/0082807 A1 | 3/2009 | Miller et al. |
| 2009/0105761 A1 | 4/2009 | Robie |
| 2010/0121348 A1* | 5/2010 | van der Burg et al. ........ 606/232 |

* cited by examiner

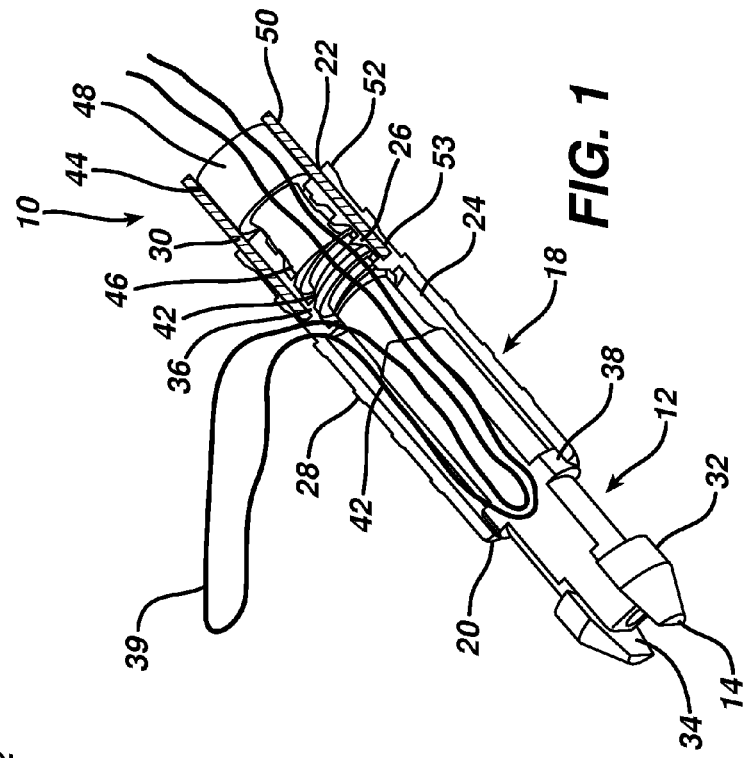
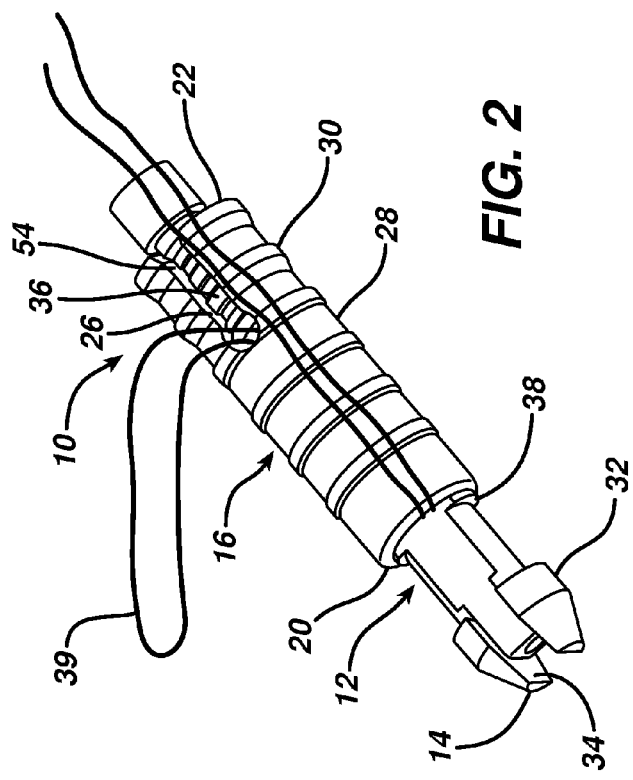

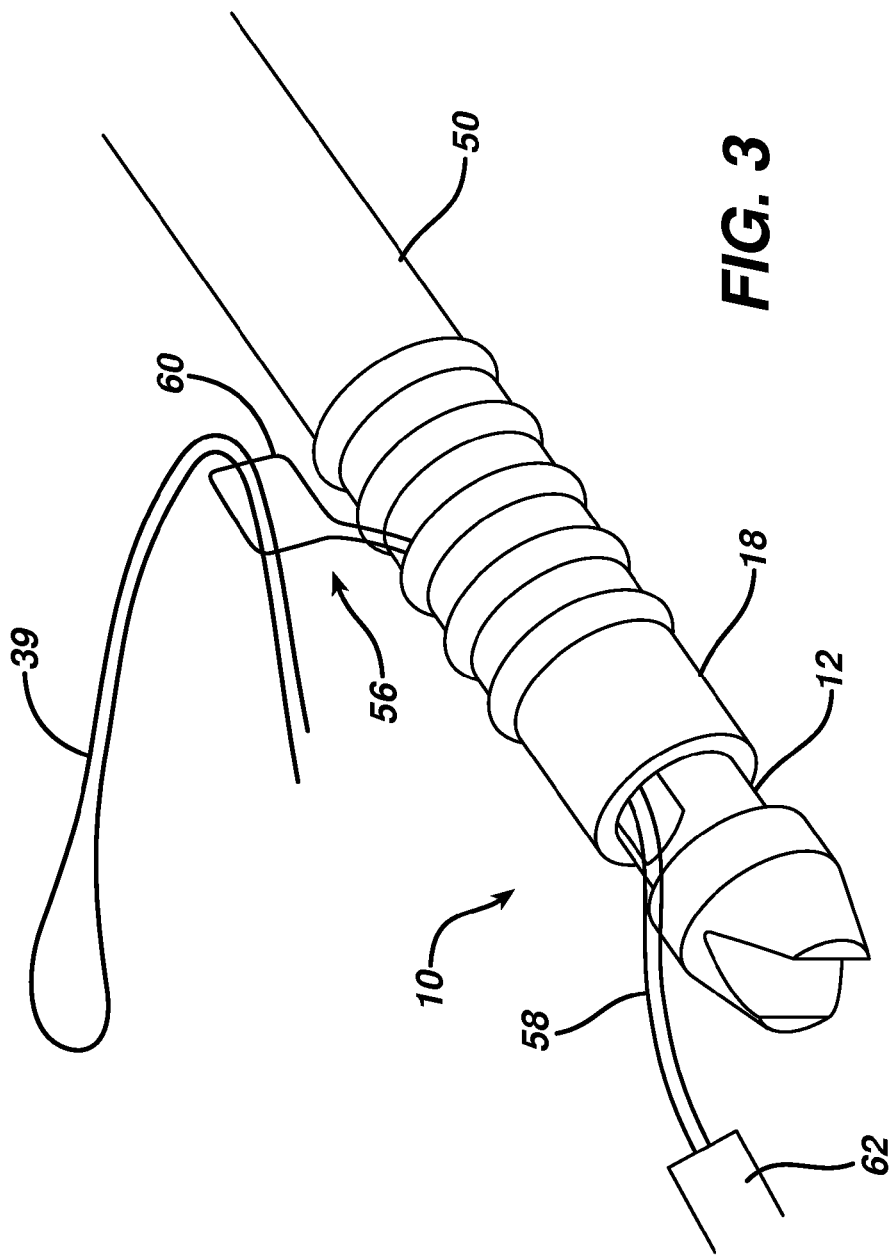

KNOTLESS SUTURE ANCHOR

CROSS REFERENCE TO RELATED APPLICATIONS

This application is a divisional application of U.S. patent application Ser. No. 12/909,355, entitled KNOTLESS SUTURE ANCHOR, filed Oct. 21, 2010, which is incorporated herein by reference.

BACKGROUND

The present application relates to suture anchors and more particularly to a knotless suture anchor.

Suture anchors have wide use in surgery particularly for reattaching soft tissue to bone. It is preferred to perform most of these surgeries endoscopically. While working through a long narrow endoscope knot tying takes on added difficulty. Accordingly it is frequently preferred to employ a suture anchor which can capture the suture without the need of the surgeon having to tie a knot. It is also preferred that while capturing the suture to lock it to the anchor that the anchor not disturb the tension on the suture. Typically the soft tissue is carefully positioned just prior to locking the suture and if the act of locking the suture causes it to move it can affect the position of the soft tissue.

SUMMARY OF THE INVENTION

A suture anchor according to the present invention comprises an outer body having a distal end a proximal end and an axial bore therethrough. An inner body is receivable within the outer body. A suture limb is captured between the inner body and the outer body by being wrapped around the inner body.

Preferably, the inner body and the outer body are formed of a bioabsorbable material, as for example a material comprising PLGA.

Preferably, the inner body and outer body are threaded together.

Preferably, the suture anchor is configured such that as the inner body is moved toward the proximal end of the outer body the proximal end of the outer body expands outwardly radially.

Preferably, the suture limb is wrapped around the inner body at least two times. Enhanced holding is provided when the suture limb is wrapped around the inner body at least five times.

Preferably, the inner body comprises at least one tab extending outwardly radially whereby to effect wrapping of the suture about the inner body upon rotation of the inner body.

Preferably, the inner body has a distal end and a proximal end and wherein the inner body proximal has outer threads which mate with inner threads on the proximal end of the outer body. Preferably, an inserter is provided having a distal end which mates with the proximal end of the inner body and which has outer inserter threads engageable with the inner threads on the outer body. Preferably, the outer body has a first configuration in which at least a portion thereof is radially contracted inwardly and a second configuration in which the portion is radially expanded outwardly, and wherein when the outer inserter threads are engaged into the outer body inner threads it holds the portion in the second configuration. Similarly, when the outer threads on the inner body are engaged into the outer body inner threads it holds the portion in the second configuration. Preferably, a naturally relaxed position of the portion is in the second configuration. Thus, when the outer body is expanded into the bone internal stresses on the outer body are minimized.

In one aspect of the invention, the suture limb passes into a space formed between the inner body and the outer body at their proximal ends, passes out of the space at their distal ends and then passes proximally along an outer surface of the outer body.

Preferably, the outer body has at its proximal end at least one axially extending slit therein whereby to relieve stresses upon radially outward expansion of the outer body proximal end.

In one aspect of the invention, at least one more suture limb is captured between the inner body and the outer body or perhaps at least three more suture limbs captured between the inner body and the outer body.

A method according to the present invention provides for attaching tissue to a bone. It comprises the steps of: passing a limb of suture from the tissue between a suture anchor outer body, which has a distal end a proximal end and an axial bore therethrough, and an inner body receivable within the outer body; inserting the outer body into the bone; sliding the suture between the inner body and the outer body to achieve a desired tension thereon or desired position of the tissue; capturing the suture limb between the inner body and the outer body, by wrapping at least a segment of the suture limb about the inner body, to prevent sliding of the suture limb therebetween.

Preferably, the distance between the tissue and the anchor stays substantially the same during the step of capturing.

Preferably, the suture limb is wrapped around the inner body at least two times.

Preferably, the inner body has at least one radially extending projection and the step of wrapping comprises rotating the inner body within the outer body during which the projection engages the suture limb to cause it to wrap about the inner body.

Preferably, the method further comprises the step of radially expanding at least a portion of the outer body to engage the suture anchor into the bone. For instance when a proximal end of the inner body has outer threads and the proximal end of the outer body has mating inner threads then the step of radially expanding can comprise engaging the inner body outer threads with the outer body inner threads.

BRIEF DESCRIPTION OF THE DRAWINGS

FIG. 1 is a perspective cut-away view of a suture anchor according to the present invention;

FIG. 2 is a perspective view of the suture anchor of FIG. 1;

FIG. 3 is a perspective view of the suture anchor of FIG. 1 pre-loaded with a suture capture device;

DETAILED DESCRIPTION

Figure 4:
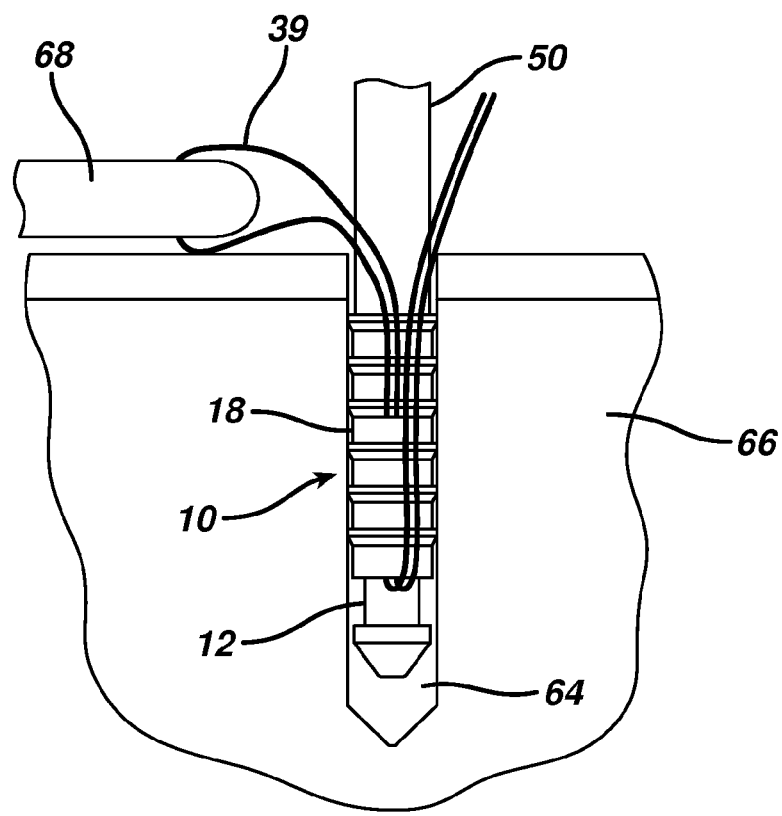
FIG. 4 is a side elevation view in cut-away of soft tissue and associated bone showing initial insertion of the suture anchor of FIG. 1.

FIG. 1 depicts a suture anchor 10 according to the present invention. It comprises in gross an inner body 12 having a distal end 14 and proximal end 16 and a cannulated outer body 18 having a distal end 20, proximal end 22 and a cannulation 24 therethrough. Towards the outer body proximal end 22 the cannulation 24 bears internal threads 26 which decrease in internal diameter at the proximal end 22. On its exterior surface 28 the outer body 18 bears barb shaped annular flanges 30 to assist in bone fixation.

The inner body 12 has an annular flange 32 at its distal end 14 with a groove 34 therethrough passing over the distal end 14. At its proximal end 16 the inner body 12 has exterior threads 36 which mate with the inner body threads 26. A pair of radially extending projections 38 extend from the inner body 12 toward the outer body 18 at its distal end 20. The tolerance between the projections 38 and the outer body 18 should be close enough to prevent suture 39 from passing therebetween.

A tool receiving recess 40 on the inner body proximal end 16 mates with a driver head 42 (such as for instance a hex driver) on a distal end of a driver 44. Just proximal thereof on the driver 44 are threads 46 which mate with the threads 26 on the outer body 18. The threads 46 have a reduced major diameter at a proximal portion 48 which in its starting configuration as shown in FIG. 1 sits adjacent the decreased internal diameter of the outer body thread 26 at their proximal end 22. The driver 44 operates within a tube 50 having a distal end 52 abutting the outer body proximal end 22 with distally projecting tangs 53 extending into slots 54 in the outer body proximal end. This interface assists in maintaining the position of the anchor 10 as it is employed, by resisting both rotation and proximal withdrawal thereof.

Turning also now to FIG. 2, two or more of the stress relief slots 54 extend axially into the outer body 18 from its proximal end 22. This allows the proximal end to be made from somewhat brittle materials yet still be able to expand outwardly radially to provide fixation. Both the inner body 12 and outer body 18 are preferably formed of a bioabsorbable material such as BIOCRYL RAPIDE available from DePuy Mitek, Inc. of Raynham, Mass. BIOCRYL RAPIDE is a bioabsorbable polymer formed of homogenous blend of Tri-Calcium Phosphate (TCP) and Polylactic/polyglycolic Acid (PLGA). Other suitable materials include without limitation PEEK, PLA, titanium, stainless steel, metals, polymers and other biocompatible materials.

Turning also now to FIGS. 3 to 7, use of the suture anchor 10 will be described. The anchor 10 is sterile and packaged in bacteria proof packaging (not shown) pre-loaded onto the driver 44 and pre-loaded with a suture capture device 56 comprising an elongated filament 58 having a suture capture loop 60 at one end. One example is the CHIA PERCPASSER available from DePuy Mitek, Inc. of Raynham, Mass. The loop 60 in FIG. 3 is shown adjacent the anchor 10 for ease of display but in practice sufficient length of the filament 58 would extend from the anchor 10 to allow suture 39 to be pulled out of a cannula (not shown) through which the procedure is being endoscopically performed.

The suture 39 would be loaded into the suture capture loop 60 exterior of the patient and the cannula. A tab 62 may be placed on an opposite end of the filament 58. (This is also shown adjacent the anchor 10 for ease of display but would more conveniently be positioned outside of the cannula.) When the tab is pulled the loop 60 with the suture 39 captured therein is drawn down between the inner body 12 and outer body 18 pulling the suture 39 with it. The path of the suture 39 after passing between the inner body 12 and outer body 18 goes through the groove 34 to assist in sliding. Additional sutures can also be employed, such as additional suture loops in the suture capture loop 60 or addition suture loops each with their own suture capture device.

The anchor 10 with the suture 39 therein is now inserted into a pre-drilled hole 64 in a bone 66 to which a piece of soft tissue 68 is to be attached as shown in FIG. 4. The anchor 10 is positioned in the hole 64 such that the suture passes into the anchor 10 at one of the stress relief slots 54. The suture 39 is shown looped through the soft tissue 68 but other arrangements are possible such as extending from another anchor (not shown and typically of a different configuration than anchor 10) which is positioned in the bone 66 below the soft tissue 68 and up through the soft tissue 68 to the anchor 10, such as in a dual row rotator cuff repair. Also, the path from the soft tissue 68 through the anchor 10 could be reversed.

Figure 5:
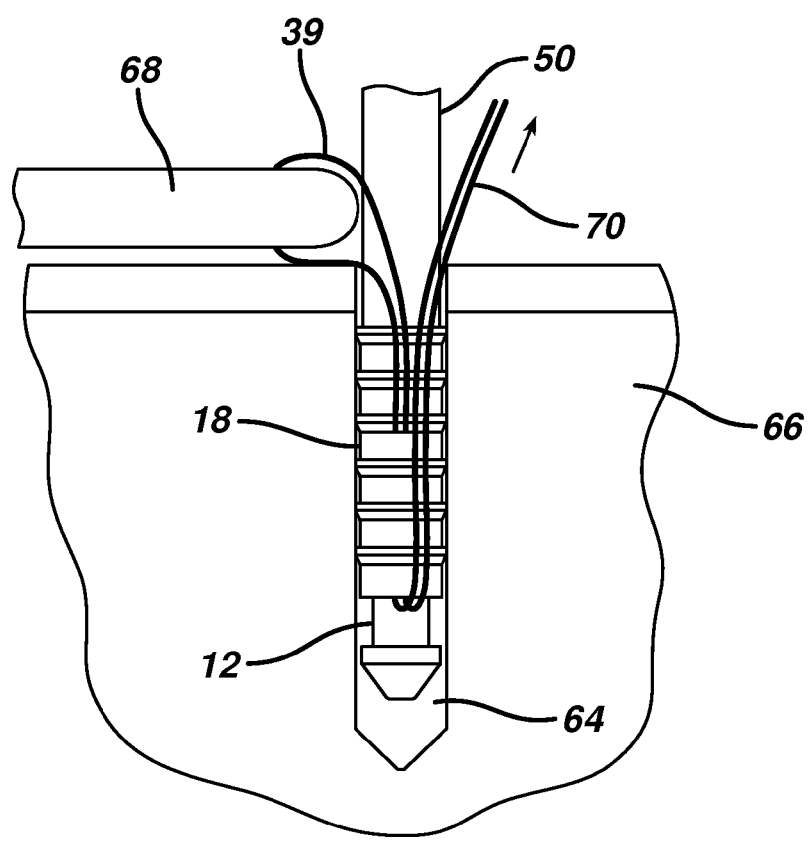
FIG. 5. is a side elevation view in cut away of the soft tissue and bone of FIG. 4 showing free ends of a suture between the soft tissue and the anchor being pulled to tension the suture and position the soft tissue.
Figure 6:
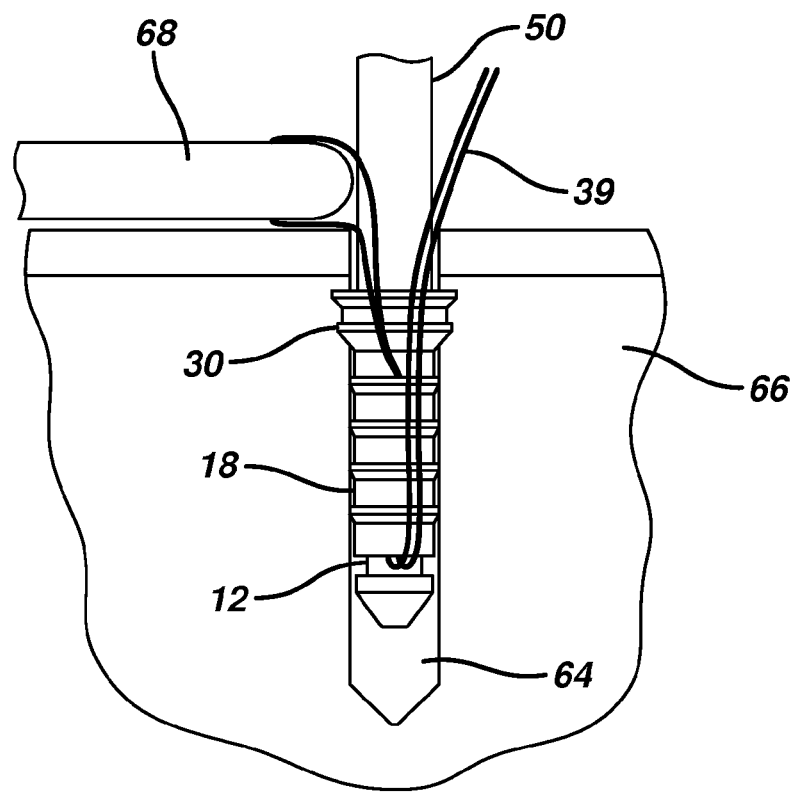
FIG. 6 is a side elevation view in cut away of the soft tissue and bone of FIG. 4 showing the anchor being actuated to lock the suture to the anchor and the anchor to the bone.
Figure 7:
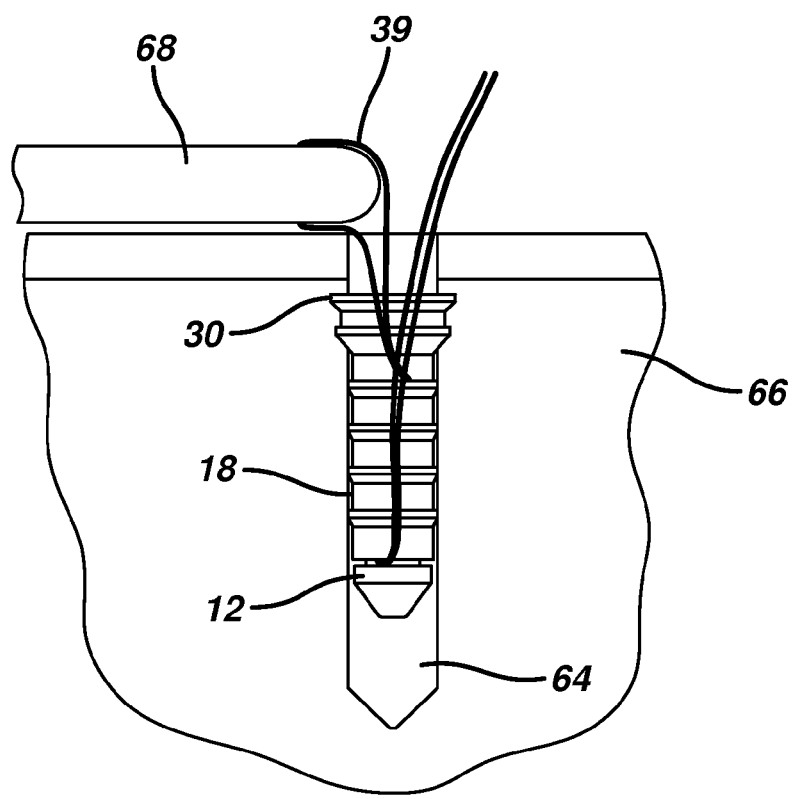
FIG. 7 is a side elevation view in cut away of the soft tissue and bone of FIG. 4 showing the anchor fully deployed.
Figure 8:
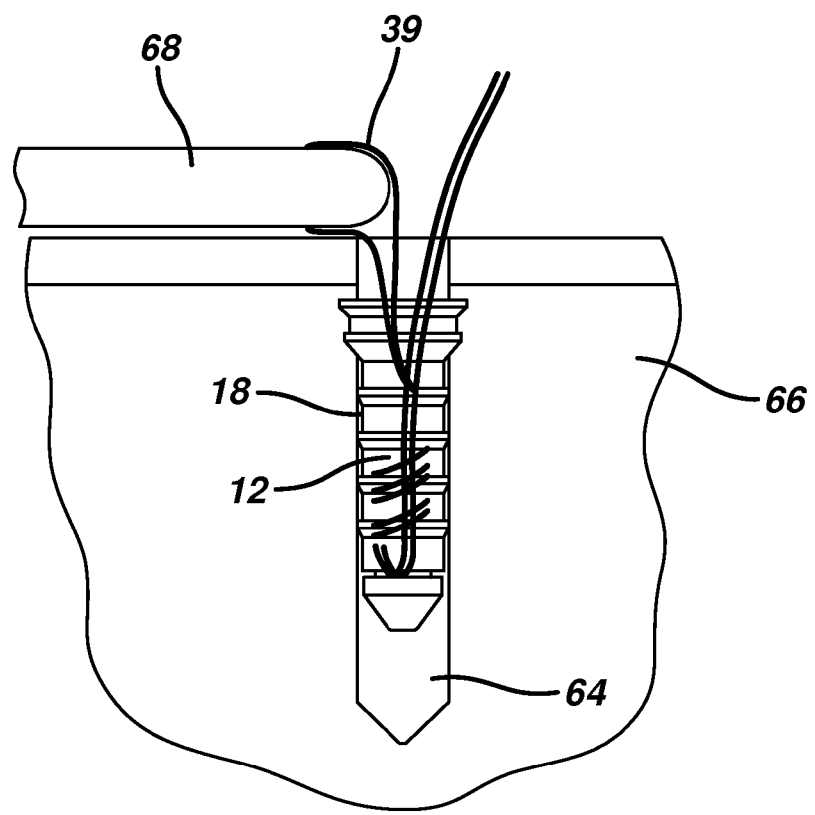
FIG. 8 is a side elevation view in cut away of the soft tissue and bone of FIG. 4 showing the anchor in partial cut-away in its fully deployed position.

Free ends 70 of the suture 39 are drawn through the anchor 10 to position the soft tissue 68 and properly tension the suture 39 (see FIG. 5). The tube 50 of the driver 44 holds the anchor 10 down and prevents rotation of the outer body 18 while the driver 44 is rotated to rotate the inner body 18 (see FIG. 6). As the threads 46 of the driver 44 pass through the reduced inner diameter proximal portion 22 of the outer body 18 it causes it to expand outwardly radially to engage the bone 66 and reduces the stress on the inner body 18. Preferably, the relaxed condition of the outer body 18 is slightly expanded radially and as it is inserted into the hole 64 it is compressed slightly inwardly; the expansion by the threads 46 move it back to its relaxed configuration thus reducing internal stress. As the rotation continues the threads 36 of the inner body move into the reduced inner diameter proximal portion 22 to keep the outer body proximal end 22 radially expanded. The projections 38 on the inner body 12 cause the suture 39 to wrap around the inner body 12. The suture 39 feeds in from the free ends 70, not from the soft tissue 68 so that the position of the soft tissue 68 and the tension on the suture 39 between the anchor 10 and the soft tissue 68 remains substantially unchanged as the inner body 12 is rotated. After sufficient rotation the driver 44 is disengaged from the anchor 10 and removed leaving the suture 39 locked to the anchor 10 by virtue of its being wrapped around the inner body 12 and the outer body proximal end 22 is expanded outwardly into the bone 66 to lock the anchor 10 thereto (see FIGS. 7 and 8). Tests have shown three to five turns providing good locking of the suture 39.

Figure 9:
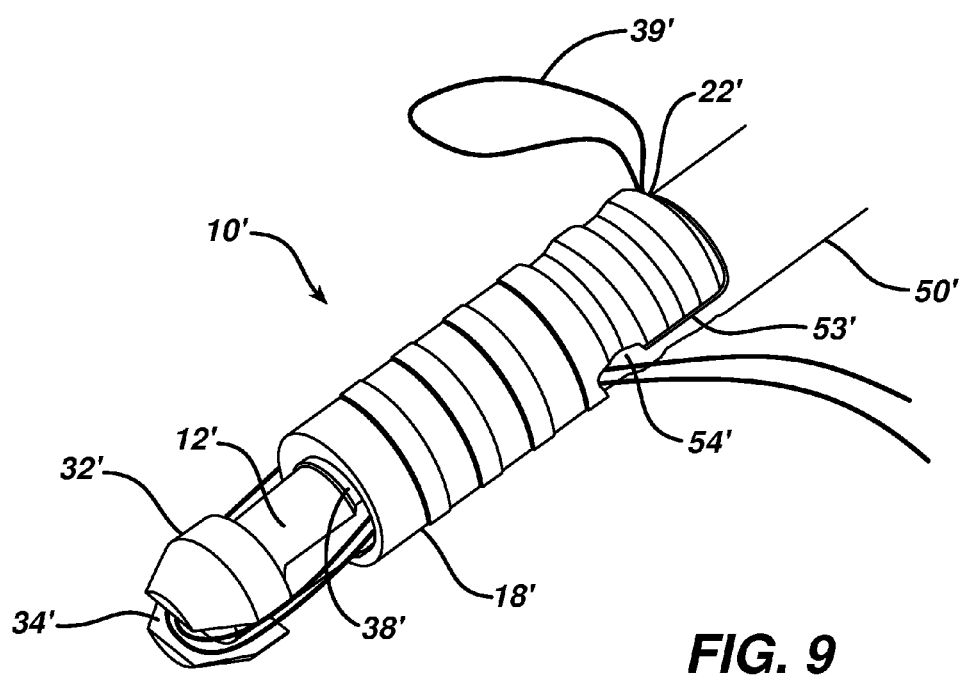
FIG. 9 is a perspective view of a further embodiment of a suture anchor according to the present invention.
Figure 10:
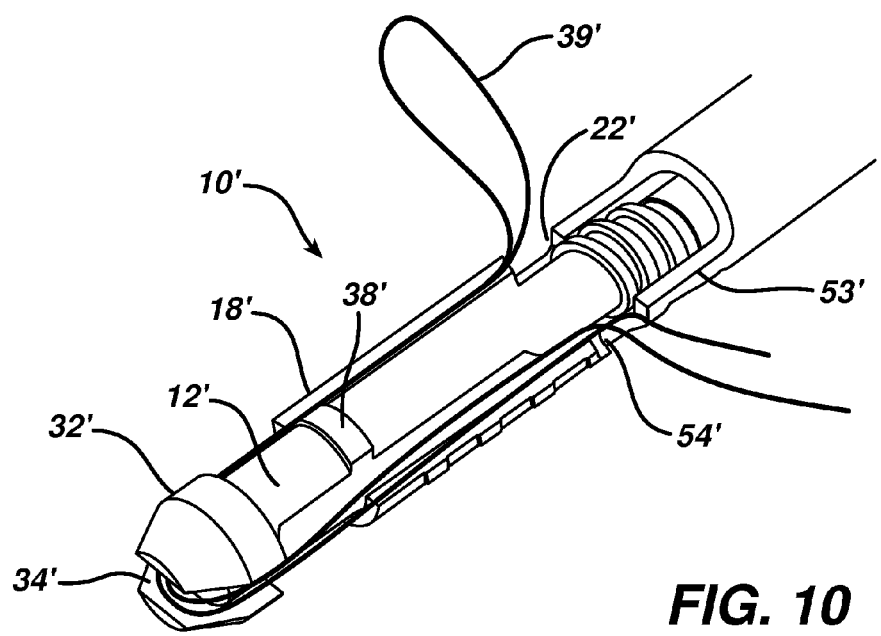
FIG. 10 is a perspective cut-away view of the suture anchor of FIG. 9.

FIGS. 9 and 10 illustrate a further preferred embodiment of the invention which is essentially similar to that depicted in FIGS. 1 and 2. Like parts are denoted with like numerals with the addition of a prime symbol ('). It comprises a suture anchor 10' having an inner body 12' and cannulated outer body 18' having a short internal thread 24'. The inner body 12' has an annular flange 32' at its distal end 14' with a groove 34'. It also carries radially extending projections 38'. FIG. 9 especially more clearly illustrates how a driver receiving tube 50' abuts a proximal end 22' of the outer body 18' with distally projecting tangs 53' extending into stress relief slots 54'. A loop of suture 39' has free ends which pass into the outer body 18' from its proximal end 22', preferably through one of the stress relief slots 54', passes down between the inner body 12' and outer body 18' and between the projections 38', out of the outer body 18' through its distal end 20', through the groove 34' on the inner body 12' at its distal end 14' and then back into the outer body 18' between it and the inner body 12' and also again between the projections 38" and finally exit through the opposing stress relief slot 54'. This embodiment is used similarly to the previous one. However, the groove 34' assists in wrapping the suture 39' around the inner body 12' and one could even dispense with the projections 38' due to the wrapping action provided by the groove 34'.

Various modifications and alterations of this invention will be apparent to those skilled in the art without departing from the scope and spirit of this invention. It should be understood that the invention is not limited to the embodiments disclosed herein, and that the claims should be interpreted as broadly as the prior art allows.

What is claimed is:

1. A method of attaching tissue to a bone comprising the steps of:
    passing a limb of suture from the tissue between a suture anchor outer body, which has a distal end, a proximal end and an axial bore therethrough, and an inner body receivable within the outer body;
    inserting the outer body into the bone;
    sliding the suture between the inner body and the outer body to achieve a desired tension thereon or desired position of the tissue;
    capturing the suture limb between the inner body and the outer body, by wrapping at least a segment of the suture limb about the inner body, to prevent sliding of the suture limb therebetween; and
    radially expanding at least a portion of the outer body to engage the suture anchor into the bone by moving the inner body proximally into the outer body by engaging outer threads on the proximal end of the inner body with mating inner threads on the proximal end of the outer body.

2. A method according to claim 1 wherein the distance between the tissue and the anchor stays substantially the same during the step of capturing.

3. A method according to claim 1 wherein the suture limb is wrapped around the inner body at least two times.

4. A method according to claim 1 wherein the inner body has at least one radially extending projection and the step of wrapping comprises rotating the inner body within the outer body during which the projection engages the suture limb to cause it to wrap about the inner body.

5. A method according to claim 1 wherein rotation of the inner body effects simultaneously the step of wrapping the suture limb about the inner body and the step of engaging the outer threads on the inner body with the inner threads on the outer body.

\* \* \* \* \*